US012758745B2

(12) United States Patent
Kitaoka et al.

(10) Patent No.: US 12,758,745 B2
(45) Date of Patent: Oct. 13, 2026

(54) CATHETER SHAPE RETAINER

(71) Applicant: TERUMO KABUSHIKI KAISHA, Tokyo (JP)

(72) Inventors: Takashi Kitaoka, Hadano city (JP); Taishi Niimi, Hadano city (JP); Takayuki Uchida, Hiratsuka-city (JP); Yu Osawa, Ebina city (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 175 days.

(21) Appl. No.: 18/898,192

(22) Filed: Sep. 26, 2024

(65) Prior Publication Data

US 2025/0018157 A1 Jan. 16, 2025

Related U.S. Application Data

(63) Continuation of application No. PCT/JP2023/009222, filed on Mar. 10, 2023.

(30) Foreign Application Priority Data

Mar. 28, 2022 (JP) ................................. 2022-052429

(51) Int. Cl.
*A61M 25/06* (2006.01)
*A61M 25/01* (2006.01)

(52) U.S. Cl.
CPC .................................. *A61M 25/06* (2013.01)

(58) Field of Classification Search
CPC .............................. A61M 25/01; A61M 25/06
See application file for complete search history.

(56) References Cited

FOREIGN PATENT DOCUMENTS

| | | | |
|---|---|---|---|
| JP | 2002325848 | A | 11/2002 |
| JP | 2007236819 | A | 9/2007 |
| JP | 2013070872 | A | 4/2013 |

OTHER PUBLICATIONS

International Search Report (PCT/ISA/210) with translation and Written Opinion (PCT/ISA/237) mailed on Apr. 11, 2023, by the Japan Patent Office as the International Searching Authority for International Application No. PCT/JP2023/009222. (8 pages).

English language translation of the International Search Report (Form PCT/ISA/210) and the Written Opinion of the International Searching Authority (Form PCT/ISA/237) issued Apr. 11, 2023, by the Japanese Patent Office in corresponding International Application No. PCT/JP2023/009222. (5 pages).

*Primary Examiner* — Brian T Gedeon
(74) *Attorney, Agent, or Firm* — .Buchanan Ingersoll & Rooney PC

(57) ABSTRACT

A catheter shape retainer includes a retainer main body inserted and disposed in an inner lumen of a catheter to retain a cylindrical shape of the catheter, and a movement restrictor disposed closer to a distal portion of the retainer main body than a proximal portion of the retainer main body to restrict the catheter from moving toward the proximal portion of the retainer main body. When a portion of the retainer main body including the distal portion of the retainer main body is inserted into a living body, a portion of the retainer main body located outside the living body has a length longer than a total length of a puncture device.

18 Claims, 6 Drawing Sheets

CATHETER SHAPE RETAINER

CROSS-REFERENCES TO RELATED APPLICATIONS

This application is a continuation of International Application No. PCT/JP2023/009222 filed on Mar. 10, 2023, which claims priority to Japanese Application No. 2022-052429 filed on Mar. 28, 2022, the entire content of both of which is incorporated herein by reference.

TECHNOLOGICAL FIELD

The present disclosure generally relates to a catheter shape retainer that retains a cylindrical shape of an elongated catheter that is inserted into a living body.

BACKGROUND DISCUSSION

Development of a brain disease such as cerebral infarction blocks blood flow for supplying oxygen to brain cells, which may cause a risk of damaging the brain cells. This is why cerebral infarction requires early reperfusion of blood flow. However, patients who meet the conditions for high-level evidence-based hyperacute phase treatment (for example, administration of tissue plasminogen activator (t-PA) and mechanical thrombectomy (MT)) currently in clinical practice account for a relatively small percentage. Therefore, many patients have no choice but to select conservative therapy.

As a treatment for cerebral infarction, it has been proposed to inject oxygen-rich liquid such as oxygenated cerebrospinal fluid into the medullary cavity of a patient and directly supply oxygen to oxygen-deficient brain cells. In this proposal, cerebral infarction is treated by inserting a catheter into the spinal canal from a lumbar vertebra, delivering a distal portion to a spot near the brain, injecting artificial cerebrospinal fluid as oxygen-rich liquid, and aspirating cerebrospinal fluid by a portion on the proximal side.

In this treatment, it is desired to keep the thickness of the catheter small to secure a lumen (that is, a channel) of the catheter while keeping the outside diameter of the catheter small to reduce invasive stress given to the patient. However, keeping the thickness of the catheter small and the outside diameter of the catheter small easily causes kinks. For example, in a case where a catheter is inserted into a living body through an inner lumen of a puncture device provided with a needle that pierces the living body, the catheter easily generates kinks near a distal end of the puncture device. In order to insert a medical instrument into a body cavity from a puncture hole opened on the body surface, Japanese Patent Application Publication No. 2013-70872 A discloses a dilator for expanding the puncture hole.

In addition, a longer catheter increases resistance of fluid flowing through a lumen of the catheter and decreases flow velocity. Therefore, it is desired to shorten the catheter and suppress the channel resistance. However, if a catheter has a small length, at the time of removing a puncture device after inserting the catheter into a living body through an inner lumen of the puncture device, it may be difficult to remove the puncture device while maintaining the position of the catheter. In other words, with a short catheter, an operator or the like may not be able to hold the catheter during removal of the puncture device, and the catheter may be shifted to the proximal side along with the removal of the puncture device.

SUMMARY

A catheter shape retainer is disclosed that enables kink prevention and removal of a puncture device while maintaining the position of a catheter.

A catheter shape retainer according to the present disclosure that passes through an inner lumen of a puncture device piercing a living body and retains a cylindrical shape of an elongated catheter inserted into the living body, the catheter shape retainer including: a retainer main body inserted and disposed in an inner lumen of the catheter to retain the cylindrical shape of the catheter; and a movement restrictor disposed closer to a distal portion of the retainer main body than a proximal portion of the retainer main body to restrict the catheter from moving toward the proximal portion of the retainer main body over the movement restrictor, wherein, when a portion of the retainer main body including the distal portion is inserted into the living body, a portion of the retainer main body located outside the living body has a length longer than a total length of the puncture device.

According to the catheter shape retainer of the present disclosure, the retainer main body is inserted and disposed in the inner lumen of the catheter to retain the cylindrical shape of the catheter, whereby the catheter is prevented from kinking near, for example, a distal end of the puncture device when the catheter is inserted into the living body. In addition, the puncture device is removed prior to the removal of the catheter shape retainer from the inner lumen of the catheter, which eliminates the kink-causing fulcrum (that is, the distal end of the puncture device) and prevents the catheter from kinking after the catheter is inserted into the living body.

Furthermore, the movement restrictor is disposed closer to the distal portion than the proximal portion of the retainer main body to restrict the catheter from moving toward the proximal portion of the retainer main body over the movement restrictor. When the portion of the retainer main body including the distal portion is inserted into the living body, the portion of the retainer main body located outside the living body has a length longer than the total length of the puncture device, which enables an operator or the like to hold the retainer main body during removal of the puncture device. During the removal of the puncture device, the retainer main body is held by the operator or the like, and the movement restrictor disposed in the retainer main body restricts the catheter from moving toward the proximal portion. Therefore, the use of the catheter shape retainer according to the present disclosure enables the operator or the like to remove the puncture device while maintaining the position of the catheter.

In the catheter shape retainer according to the present disclosure, the movement restrictor preferably has an outside diameter larger than an inside diameter of the catheter and smaller than an inside diameter of the inner lumen of the puncture device.

In the catheter shape retainer according to the present disclosure, the outside diameter of the movement restrictor is larger than the inside diameter of the catheter, and the movement restrictor functions as a stopper for stopping the catheter from moving toward the proximal portion, whereby the catheter is more reliably restricted from moving toward the proximal portion of the retainer main body over the movement restrictor. In addition, the outside diameter of the movement restrictor is smaller than the inside diameter of the inner lumen of the puncture device, which enables the operator or the like to remove the puncture device easily by moving the puncture device toward the proximal portion of the retainer main body while the retainer main body is inserted and disposed in the inner lumen of the catheter.

In the catheter shape retainer according to the present disclosure, the distal portion of the retainer main body is preferably more flexible than the other portion of the retainer main body.

The catheter shape retainer according to the present disclosure prevents the distal portion of the retainer main body from damaging a living tissue when the portion of the retainer main body including the distal portion is inserted into the living body.

A system configured to pierce a living body, the system comprising: a puncture device configured to pierce the living body; an elongated catheter configured to be inserted into an inner lumen of the puncture device and into the living body; a catheter shape retainer configured to be inserted into an inner lumen of the catheter, the catheter shape retainer including a retainer main body and a movement restrictor disposed closer to a distal portion of the retainer main body than a proximal portion of the retainer main body to restrict the catheter from moving toward the proximal portion of the retainer main body over the movement restrictor.

A method is disclosed for retaining a cylindrical shape of an elongated catheter inserted into a living body, the method comprising: piercing a living body with a puncture device; inserting a catheter into an inner lumen of the puncture device; and inserting a catheter shape retainer through an inner lumen of the catheter to retain the cylindrical shape of the catheter, the catheter shape retainer including a retainer main body and a movement restrictor disposed closer to a distal portion of the retainer main body than a proximal portion of the retainer main body to restrict the catheter from moving toward the proximal portion of the retainer main body over the movement restrictor, and when a portion of the retainer main body including the distal portion of the retainer main body is inserted into the living body, a portion of the retainer main body located outside of the living body has a length longer than a total length of the puncture device.

According to the present disclosure, it is possible to provide a catheter shape retainer that enables kink prevention and removal of a puncture device while maintaining the position of a catheter.

DETAILED DESCRIPTION

Figure 1:
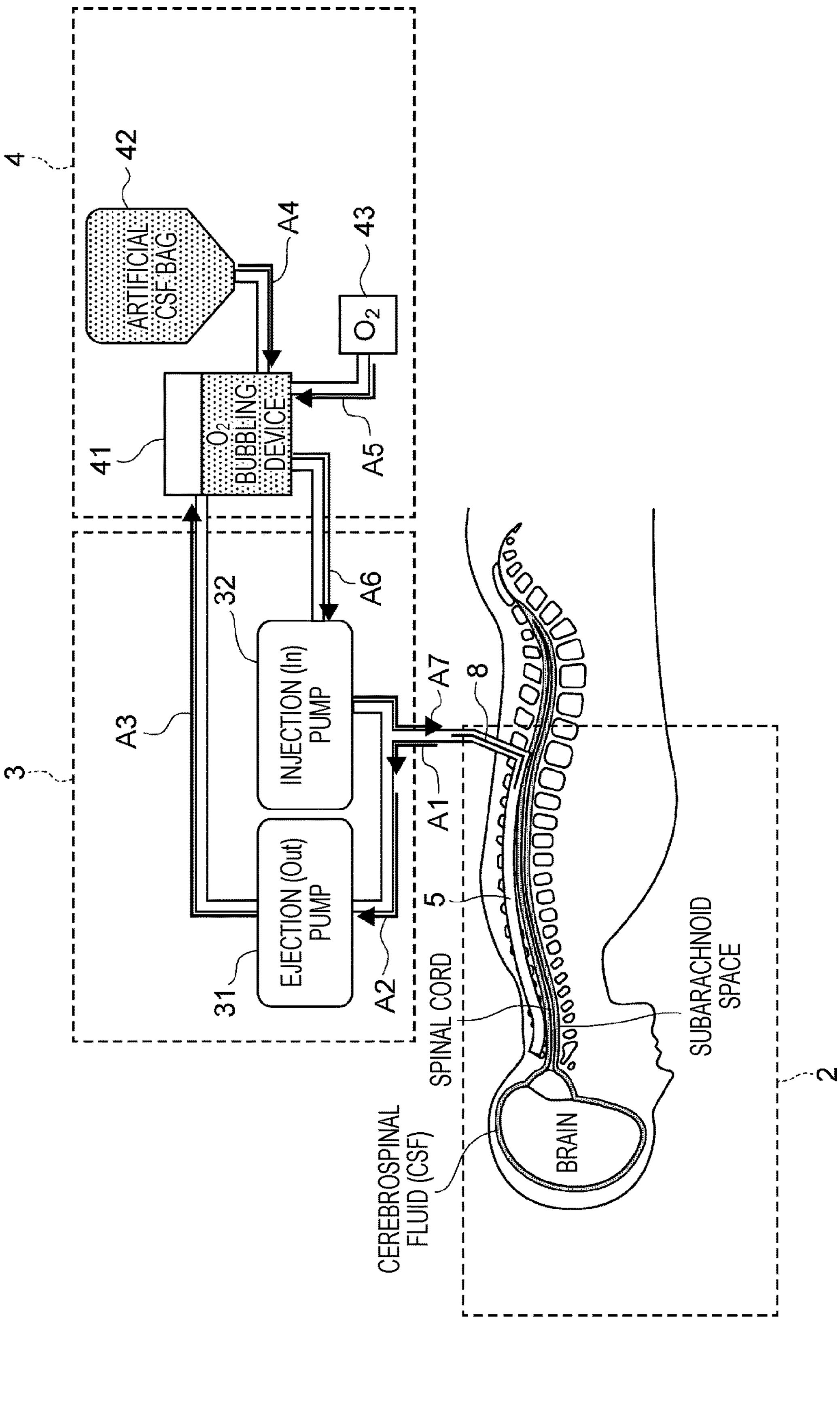
FIG. 1 is a block diagram illustrating an outline of a brain disease treatment system that employs a catheter shape retainer according to this embodiment.

Hereinafter, a preferred embodiment of the present disclosure will be described in detail with reference to the drawings, including technical contents (operation method, operation, and handling procedures).

The following embodiment is a preferred specific example of the present disclosure, and various technically preferable limitations are given. However, it should be noted that the scope of the present disclosure is not limited to these aspects unless otherwise noted. Furthermore, in the drawings, similar components are denoted by the same reference numerals and details of the similar components denoted by the same reference numerals will be appropriately omitted.

FIG. 1 is a block diagram illustrating an outline of a brain disease treatment system that employs a catheter shape retainer according to this embodiment.

Figure 2:
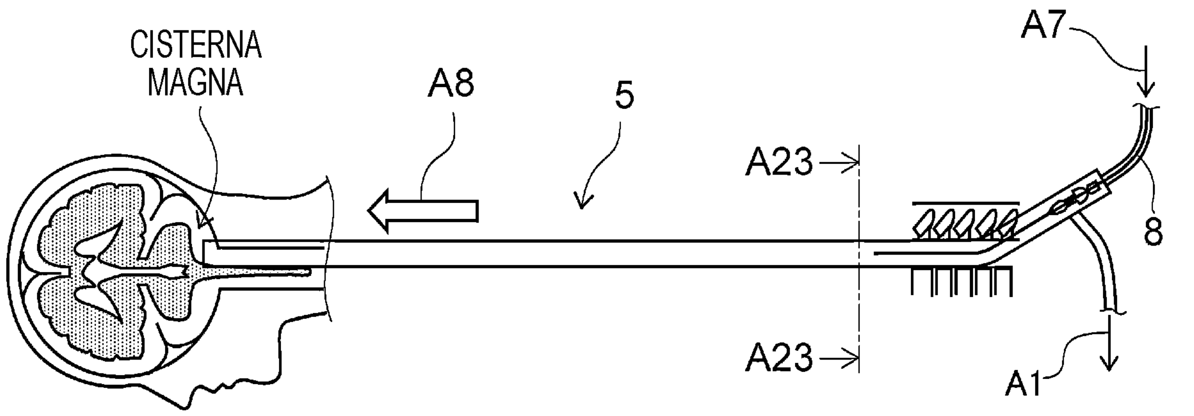
FIG. 2 is a schematic view illustrating a catheter retained by the catheter shape retainer according to this embodiment.

FIG. 2 is a schematic view illustrating a catheter retained by the catheter shape retainer according to this embodiment.

Figure 3:
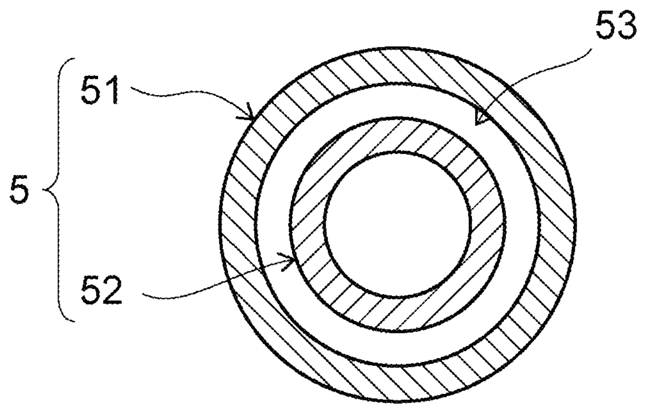
FIG. 3 is a cross-sectional view illustrating a specific example of the catheter used in the brain disease treatment system.

FIG. 3 is a cross-sectional view illustrating a specific example of the catheter used in the brain disease treatment system.

Note that FIG. 3 is a cross-sectional view taken along section A23-A23 illustrated in FIG. 2. For purpose of illustration, the catheter shape retainer according to this embodiment is omitted in FIG. 3.

A catheter shape retainer 8 according to this embodiment retains a cylindrical shape of an elongated catheter 5 that is inserted into a living body. The catheter 5 can be used, for example, in a brain disease treatment system. However, the catheter 5 is not limited to the use in a brain disease treatment system. The catheter 5 in this embodiment is illustrated as a member used in a brain disease treatment system.

As illustrated in FIG. 1, the brain disease treatment system using the catheter shape retainer 8 according to this embodiment includes a spinal subarachnoid space catheter system 2, a pump system 3, and an oxygenation mechanism 4. The catheter 5 is used in the spinal subarachnoid space catheter system 2.

When the catheter 5 is used in the brain disease treatment system, as illustrated in FIG. 3, the catheter 5 has a structure with two coaxially arranged tubes in which a tube for injecting liquid (injection tube 52) is placed in an inner lumen of a tube for ejecting cerebrospinal fluid (ejection tube 51). For example, with the catheter 5 having the structure illustrated in FIG. 3, the catheter shape retainer 8 according to this embodiment retains a cylindrical shape of the ejection tube 51 when the ejection tube 51 is inserted into the living body. However, as described above, the catheter 5 is not limited to the use in a brain disease treatment system, and a tube that has a cylindrical shape retained by the catheter shape retainer 8 is not limited to the ejection tube 51.

The injection tube 52 placed in the inner lumen of the ejection tube 51 can be inserted, for example, into the subarachnoid space from a spot near the lumbar vertebrae of a patient in the lateral decubitus position and delivered to a spot near the cisterna magna, followed by injecting oxygen-rich liquid (oxygenated cerebrospinal fluid in this embodiment) from a distal portion into cerebrospinal fluid (CSF) in the subarachnoid space. The ejection tube 51 placed on the outer side of the injection tube 52 stays at the lumbar vertebrae near the insertion site and aspirates the cerebrospinal fluid in the subarachnoid space, thereby ejecting the cerebrospinal fluid to the outside of the patient's body. The oxygen-rich liquid according to this embodiment is an example of the "liquid" of the present disclosure.

The pump system 3 can include an ejection pump 31 and an injection pump 32. As indicated by arrows A1, A2, and A3 in FIG. 1, the ejection pump 31 aspirates the cerebrospinal fluid through the ejection tube 51 of the catheter 5 and sends the cerebrospinal fluid to the oxygenation mechanism 4. As indicated by arrows A6 and A7 in FIG. 1, the injection pump 32 aspirates the oxygen-rich liquid supplied from the oxygenation mechanism 4 and injects the liquid into the cerebrospinal fluid through the injection tube 52 of the catheter 5.

In addition to a method using two pumps, the ejection pump 31 and the injection pump 32, as in this embodiment, the liquid may be injected and ejected with one pump. Alternatively, the liquid may be injected with a pump but ejected naturally or vice versa, that is, the liquid may be ejected with a pump but injected naturally. Alternatively, the liquid may be injected and ejected without any pump but with an intravenous drip using potential energy.

The oxygenation mechanism 4 can include an oxygen bubbling device 41, an artificial cerebrospinal fluid bag 42, and an oxygen supply source 43. The artificial cerebrospinal fluid bag 42 stores artificial cerebrospinal fluid (aCSF) and supplies the artificial cerebrospinal fluid to the oxygen bubbling device 41 as indicated by an arrow A4 illustrated in FIG. 1. The artificial cerebrospinal fluid can be, for example, liquid containing lactated Ringer's solution. The oxygen supply source 43 supplies oxygen to the oxygen bubbling device 41 as indicated by an arrow A5 in FIG. 1. The oxygen bubbling device 41 mixes the cerebrospinal fluid supplied from the ejection pump 31, the artificial cerebrospinal fluid supplied from the artificial cerebrospinal fluid bag 42, and the oxygen supplied from the oxygen supply source 43 and generates oxygenated cerebrospinal fluid, thereby supplying the oxygenated cerebrospinal fluid as oxygen-rich liquid to the injection pump 32 as indicated by an arrow A6 in FIG. 1.

In this embodiment, the oxygenation mechanism 4 uses the oxygen bubbling device 41. Alternatively, a hollow fiber may be immersed in cerebrospinal fluid and oxygen may be allowed to pass through the hollow fiber so as to oxygenate the cerebrospinal fluid through pores on the surface of the hollow fiber.

As illustrated in FIG. 2, the catheter 5 is inserted into the subarachnoid space from a spot near the lumbar vertebrae of a patient. The distal portion of the injection tube 52 of the catheter 5 can be delivered to a spot, for example, near the cisterna magna of the patient. As indicated by an arrow A8 illustrated in FIG. 2, the oxygen-rich liquid is sent to the distal portion of the injection tube 52 of the catheter 5 and injected into the cerebrospinal fluid in the subarachnoid space. An arrow A1 illustrated in FIG. 2 corresponds to the arrow A1 illustrated in FIG. 1. An arrow A7 illustrated in FIG. 2 corresponds to the arrow A7 illustrated in FIG. 1.

However, as described above, the catheter 5 is not limited to the use in a brain disease treatment system. In other words, the distal portion of the injection tube 52 of the catheter 5 is not limitedly delivered to a spot near the cisterna magna of a patient.

Figure 4:
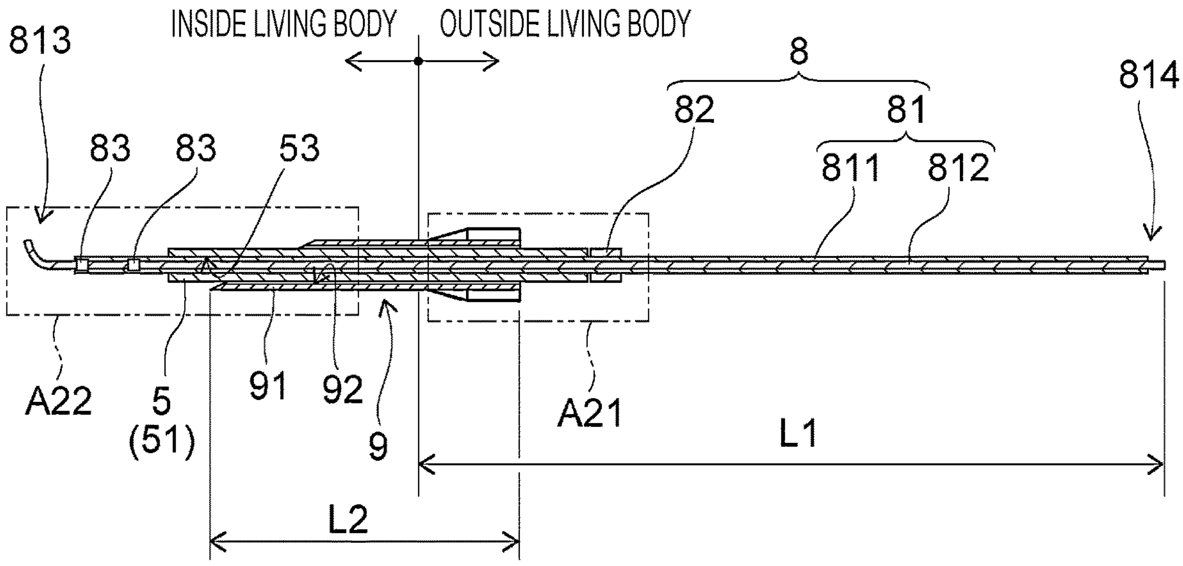
FIG. 4 is a cross-sectional view illustrating the catheter shape retainer according to this embodiment.

FIG. 4 is a cross-sectional view illustrating the catheter shape retainer according to this embodiment.

As illustrated in FIG. 4, the catheter shape retainer 8 according to this embodiment passes through an inner lumen 92 of a puncture device 9 and is inserted into a living body. The puncture device 9 can include a needle 91 that pierces the living body. However, the puncture device 9 does not necessarily have the needle 91. For example, like a dilator, the puncture device 9 may have a tapered distal portion.

The catheter shape retainer 8 includes a retainer main body 81 and a movement restrictor 82.

The retainer main body 81 includes a first body 811 and a second body 812, and as illustrated in FIG. 4, the retainer main body 81 is inserted and disposed in an inner lumen 53 of the ejection tube 51 of the catheter 5 to retain the cylindrical shape of the ejection tube 51 of the catheter 5. The first body 811 has a tubular shape and has a lumen. An example of a material for the first body 811 can include, for example, high density polyethylene (HDPE). When the first body 811 is subjected to surface treatment with fluorine-based resin such as Teflon®, the outer surface of the first body 811 is prevented from adhering to the inner surface of the ejection tube 51 of the catheter 5, which enables the first body 811 to move smoothly in the inner lumen 53 of the ejection tube 51 of the catheter 5. The second body 812 penetrates the lumen of the first body 811 and is placed in the lumen of the first body 811. As illustrated in FIG. 4, at a distal portion 813 and a proximal portion 814 of the retainer main body 81, the second body 812 is exposed outward from the first body 811.

The second body 812 is more flexible than the first body 811. For example, the second body 812 is formed of a material softer than that of the first body 811. Alternatively, the second body 812 has a more flexible structure than the structure of the first body 811. Note that the retainer main body 81 does not necessarily have the first body 811 and the second body 812 and may be formed of one member. In a case where the retainer main body 81 is formed of one member, the distal portion 813 of the retainer main body 81 is tapered to be more flexible than the portion other than the distal portion 813 of the retainer main body 81.

The second body 812 may employ a material that may be used as a core material such as wire and rod. When a wire is used as the second body 812, examples of the material for the second body 812 can include various metal materials such as, for example, stainless steel (all kinds of SUS such as SUS 304, SUS 303, SUS 316, SUS 316L, SUS 316J1, SUS 316J1L, SUS 405, SUS 430, SUS 434, SUS 444, SUS 429, SUS 430F, and SUS 302), a piano wire, a cobalt-based alloy, and an alloy exhibiting pseudoelasticity (including a superelastic alloy). Among these examples, from a viewpoint of improving torque transmission, the material for the second body 812 is preferably an alloy exhibiting pseudoelasticity (including a superelastic alloy), and more preferably a superelastic alloy.

Superelastic alloys are relatively flexible, excellent in torque transmission, resilient, and resistant to warpage. Therefore, employing a superelastic alloy for the second body 812 imparts a portion on the distal side of the retainer main body 81 with sufficient flexibility and resilience against bending. In addition, employing a superelastic alloy enhances torque transmission of the retainer main body 81 with respect to a complicatedly curved and bent blood vessel or the like and improves the traveling performance and trackability, thereby enabling more excellent operability. Even when the second body 812 is repeatedly curved, bent, and deformed, the second body 812 is resistance to warpage due to its resilience so that it is possible to prevent deterioration of operability that is attributed to the warpage of the second body 812 while using the retainer main body 81.

Furthermore, a coil may be placed on the outer periphery of a distal portion of the second body 812 to cover the distal portion of the second body 812. The coil is a member with spirally wound strands (thin wires). The coil reduces a contact surface area of the second body 812 relative to the inner wall of the ejection tube 51 of the catheter 5 and the surface of the living body. Accordingly, the sliding resistance can be reduced. The reduced sliding resistance leads to enhancement in operability of the retainer main body 81. Examples of a material for the strand of the coil include those recited above as the material for the second body 812.

The outer periphery of the distal portion of the second body 812 may be provided with a resin coating layer. In a case where the coil is placed to cover the distal portion of the second body 812, the resin coating layer is disposed on the outer periphery of the coil. Alternatively, the resin coating layer may be disposed on the entire outer periphery of the second body 812. Examples of a material for the resin coating layer can include polyolefins such as polyethylene and polypropylene, polyvinyl chloride, polyester (PET, PBT, or the like), polyamide, polyimide, polyurethane, polystyrene, polycarbonate, silicone resin, fluorine-based resin (PTFE, ETFE, or the like), and composite materials of the material for the resin coating layer as listed above. Among these examples, fluorine-based resin (or a composite material containing the same) more effectively reduces the frictional resistance (sliding resistance) between the retainer main body 81 and the inner wall of the ejection tube 51 of the catheter 5, which improves the slidability and enhances the operability of the retainer main body 81 in the inner lumen 53 of the ejection tube 51 of the catheter 5.

As illustrated in FIG. 4, a radiographic contrast medium 83 is fixed to the outer periphery of the second body 812 near the distal portion 813 of the retainer main body 81. In the catheter shape retainer 8 illustrated in FIG. 4, two radiographic contrast media 83 are disposed on the outer periphery of the second body 812. However, the number of the radiographic contrast media 83 is not limited to two and may be one or three or more. The radiographic contrast media 83 are preferably ring-shaped members having a predetermined length or linear members wound into a coil shape. Preferable examples of a material for the radiographic contrast media 83 can include gold, platinum, tungsten, iridium, alloys of gold, platinum, tungsten, and iridium, and silver-palladium alloy.

The movement restrictor 82 is disposed closer to the distal portion 813 than the proximal portion 814 of the retainer main body 81 and is fixed to the outer periphery of the retainer main body 81. Specifically, the movement restrictor 82 is fixed to the outer periphery of the first body 811. Accordingly, as illustrated in FIG. 4, from a state where the ejection tube 51 of the catheter 5 is placed on the outer periphery of the retainer main body 81 disposed closer to the distal portion 813 than the movement restrictor 82, the movement restrictor 82 can restrict the ejection tube 51 of the catheter 5 from moving toward the proximal portion 814 of the retainer main body 81. The state where the ejection tube 51 of the catheter 5 is placed on the outer periphery of the retainer main body 81 disposed closer to the distal portion 813 than the movement restrictor 82 represents that the retainer main body 81 disposed closer to the distal portion 813 than the movement restrictor 82 is inserted and disposed in the inner lumen 53 of the ejection tube 51 of the catheter 5. Details of the movement restrictor 82 will be described later with reference to FIG. 5.

As illustrated in FIG. 4, when a portion of the retainer main body 81 including the distal portion 813 is inserted into a living body, a portion of the retainer main body 81 located outside the living body has a length L1 longer than a total length L2 of the puncture device 9.

Next, the movement restrictor 82 of this embodiment will be further described with reference to the drawings.

Figure 5:
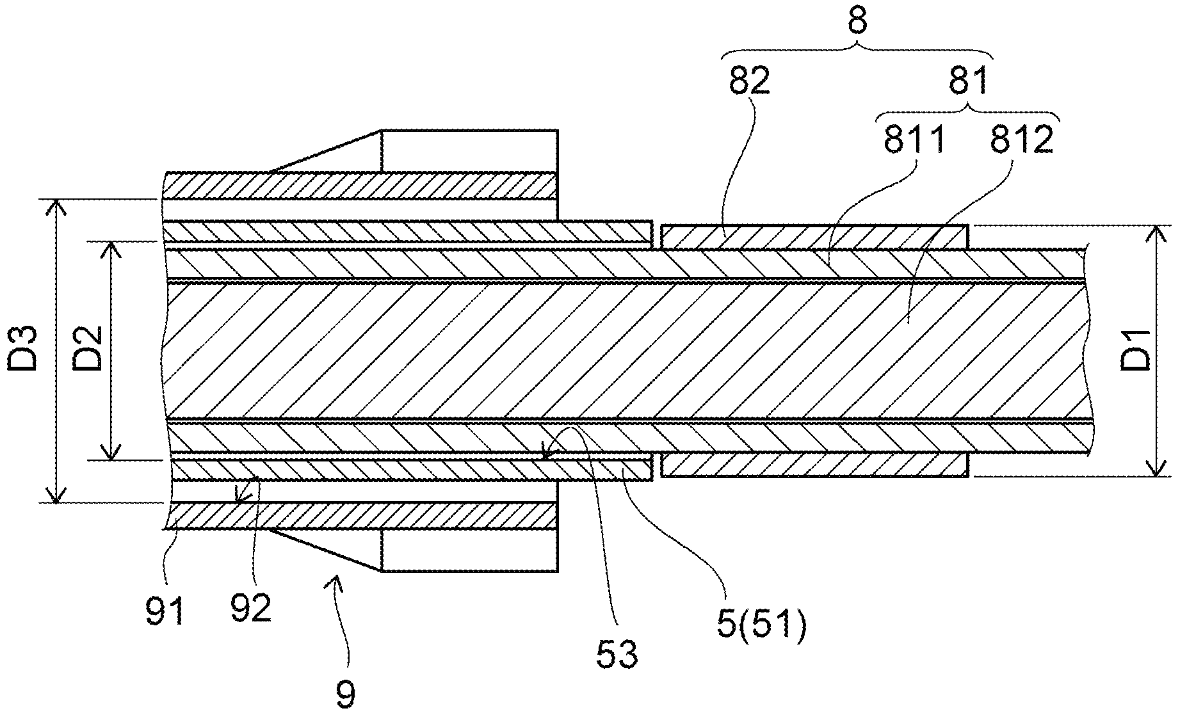
FIG. 5 is an enlarged cross-sectional view enlarging a region A21 illustrated in FIG. 4.

FIG. 5 is an enlarged cross-sectional view enlarging a region A21 illustrated in FIG. 4.

As described above with reference to FIG. 4, the movement restrictor 82 is fixed to the outer periphery of the retainer main body 81 (specifically, the first body 811) disposed closer to the distal portion 813 than the proximal portion 814 of the retainer main body 81. The movement restrictor 82 has an outside diameter D1 larger than an inside diameter D2 of the ejection tube 51 of the catheter 5. In addition, the outside diameter D1 of the movement restrictor 82 is smaller than an inside diameter D3 of the inner lumen 92 in the needle 91 or the like of the puncture device 9.

In this embodiment, the cross-sectional shape of the movement restrictor 82 is circular. However, the cross-section of the movement restrictor 82 does not necessarily have a circular shape and may have any shape as long as the movement restrictor 82 catches the ejection tube 51 of the catheter 5 and restricts the relative movement toward the proximal portion 814 of the retainer main body 81. The cross-section of the movement restrictor 82 may have an elliptic or polygonal shape or may have a rod-like shape that penetrates the retainer main body 81. Furthermore, the cross-sectional shape of the movement restrictor 82 may vary along the axial direction.

In this embodiment, the outside diameter D1 of the movement restrictor 82 is larger than the inside diameter D2 of the ejection tube 51 of the catheter 5, and the movement restrictor 82 functions as a stopper for stopping the ejection tube 51 of the catheter 5 from moving toward the proximal portion, whereby the ejection tube 51 of the catheter 5 is more reliably restricted from moving toward the proximal portion 814 of the retainer main body 81 relative to the retainer main body 81. In addition, the outside diameter D1 of the movement restrictor 82 is smaller than the inside diameter D3 of the inner lumen 92 of the needle 91 or the like of the puncture device 9, which enables an operator or the like to remove the puncture device 9 easily by moving the puncture device 9 toward the proximal portion 814 of the retainer main body 81 while the retainer main body 81 is inserted and disposed in the inner lumen 53 of the ejection tube 51 of the catheter 5.

Figure 6:
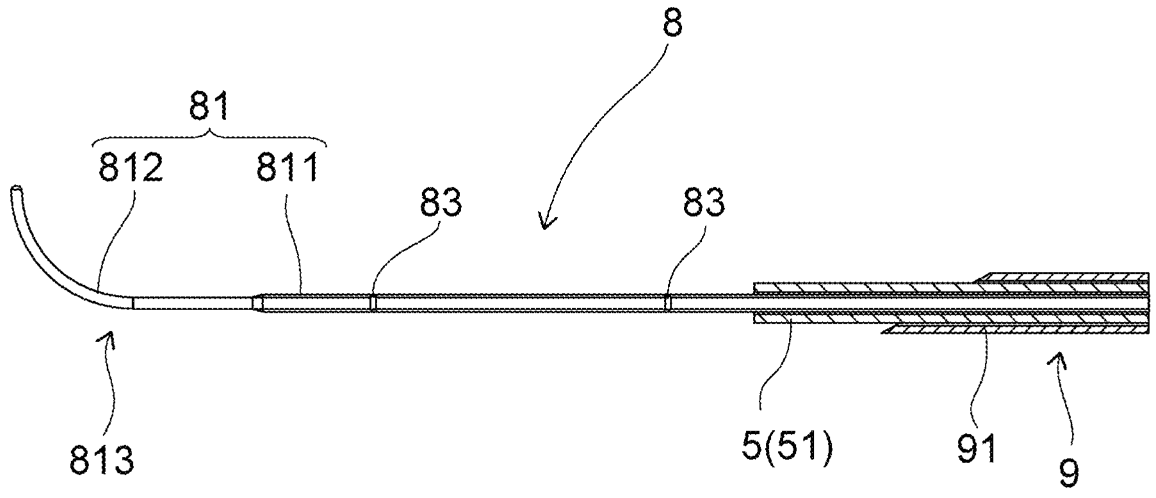
FIG. 6 is an enlarged cross-sectional view enlarging a region A22 illustrated in FIG. 4.

FIG. 6 is an enlarged cross-sectional view enlarging a region A22 illustrated in FIG. 4.

As illustrated in FIG. 6, at the distal portion 813 of the retainer main body 81, the second body 812 is exposed outward from the first body 811. Furthermore, as described above with reference to FIG. 4, the second body 812 is more flexible than the first body 811. Therefore, the distal portion 813 of the retainer main body 81 is more flexible than the portion other than the distal portion 813 of the retainer main body 81.

Accordingly, it is possible to prevent the distal portion 813 of the retainer main body 81 from damaging a living tissue when the portion of the retainer main body 81 including the distal portion 813 is inserted into the living body.

As illustrated in FIG. 6, the radiographic contrast media 83 are fixed to the outer periphery of the second body 812 near the distal portion 813 of the retainer main body 81. Accordingly, the operator or the like can insert the catheter shape retainer 8 into the living body while checking the position near the distal portion 813 of the retainer main body 81 by X-ray fluoroscopy. Note that the radiographic contrast media 83 may be fixed to the outer periphery of the first body 811.

In this manner, according to the catheter shape retainer 8 of this embodiment, the retainer main body 81 is inserted and disposed in the inner lumen 53 of the catheter 5 to retain the cylindrical shape of the catheter 5, whereby the catheter 5 is prevented from kinking near, for example, a distal end of the puncture device 9 when the catheter 5 is inserted into the living body. In addition, the puncture device 9 is removed prior to the catheter shape retainer 8, which eliminates the kink-causing fulcrum (that is, the distal end of the needle 91 of the puncture device 9) and prevents the catheter 5 from kinking after the catheter 5 is inserted into the living body.

Furthermore, the movement restrictor 82 is disposed closer to the distal portion 813 than the proximal portion 814 of the retainer main body 81 to restrict the catheter 5 from moving toward the proximal portion 814 of the retainer main body 81 relative to the retainer main body 81. Herein, when the portion of the retainer main body 81 including the distal portion 813 is inserted into the living body, the portion of the retainer main body 81 located outside the living body has the length L1 longer than the total length L2 of the puncture device 9, which configuration enables the operator or the like to hold the retainer main body 81 during removal of the puncture device 9. During the removal of the puncture device 9, the retainer main body 81 is held by the operator or the like, and the movement restrictor 82 disposed in the retainer main body 81 restricts the catheter 5 from moving toward the proximal portion. Therefore, the use of the catheter shape retainer 8 according to this embodiment enables the operator or the like to remove the puncture device 9 while maintaining the position of the catheter 5.

The embodiment of the present invention has been described above. However, the present invention is not limited to the embodiment, and various modifications can be made without departing from the scope of the claims. The configurations of the embodiment may be partially omitted or optionally combined to make different configurations from the aforementioned configurations.

For example, in the embodiment, the retainer main body 81 is illustrated as including two members, the first body 811 and the second body 812, but the retainer main body 81 may include one resin member.

The detailed description above describes embodiments of a catheter shape retainer that retains a cylindrical shape of a long catheter that is inserted into a living body. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter shape retainer configured to pass through an inner lumen of a puncture device and to pierce a living body and to retain a cylindrical shape of an elongated catheter inserted into the living body, the catheter shape retainer comprising:

a retainer main body inserted and disposed in an inner lumen of the catheter to retain the cylindrical shape of the catheter;

a movement restrictor disposed closer to a distal portion of the retainer main body than a proximal portion of the retainer main body to restrict the catheter from moving toward the proximal portion of the retainer main body over the movement restrictor; and wherein, when a portion of the retainer main body including the distal portion of the retainer main body is inserted into the living body, a portion of the retainer main body located outside the living body has a length longer than a total length of the puncture device.

2. The catheter shape retainer according to claim 1, wherein the movement restrictor has an outside diameter larger than an inside diameter of the catheter and smaller than an inside diameter of the inner lumen of the puncture device.

3. The catheter shape retainer according to claim 1, wherein the distal portion of the retainer main body is more flexible than other portions of the retainer main body.

4. The catheter shape retainer according to claim 1, wherein the retainer main body is configured to be inserted and disposed in an inner lumen of the catheter to retain the cylindrical shape of the catheter.

5. The catheter shape retainer according to claim 1, wherein the retainer main body is formed of one member, and a distal portion of the retainer main body is tapered to be more flexible than the portion other than the distal portion of the retainer main body.

6. The catheter shape retainer according to claim 1, wherein the retainer main body includes a first body and a second body, the first body having a tubular shape and a lumen, and the second body is configured to be placed in the lumen of the first body.

7. The catheter shape retainer according to claim 6, wherein the second body is exposed outward from the first body at a distal portion of the retainer main body and a proximal portion of the retainer main body.

8. The catheter shape retainer according to claim 6, wherein the second body has a more flexible structure than a structure of the first body.

9. The catheter shape retainer according to claim 6, wherein the second body is formed of a material softer than that of the first body.

10. The catheter shape retainer according to claim 6, further comprising:

a radiographic contrast medium fixed to an outer periphery of the second body on a distal portion of the retainer main body.

11. The catheter shape retainer according to claim 6, wherein the movement restrictor is fixed to the outer periphery of the first body.

12. The catheter shape retainer according to claim 1, wherein the catheter comprises an ejection tube, and the movement restrictor has an outside diameter larger than an inside diameter of the ejection tube of the catheter, and the outside diameter of the movement restrictor is smaller than an inside diameter of an inner lumen of a needle of the puncture device.

13. The catheter shape retainer according to claim 1, wherein a cross-sectional shape of the movement restrictor is circular or polygonal.

14. A system configured to pierce a living body, the system comprising:

a puncture device configured to pierce the living body;

an elongated catheter configured to be inserted into an inner lumen of the puncture device and into the living body;

a catheter shape retainer configured to be inserted into an inner lumen of the catheter, the catheter shape retainer including a retainer main body and a movement restrictor disposed closer to a distal portion of the retainer main body than a proximal portion of the retainer main body to restrict the catheter from moving toward the proximal portion of the retainer main body over the movement restrictor.

15. The system according to claim 14, wherein, when a portion of the retainer main body including the distal portion is inserted into the living body, a portion of the retainer main body located outside the living body has a length longer than a total length of the puncture device.

16. The system according to claim 14, wherein the movement restrictor has an outside diameter larger than an inside diameter of the catheter and smaller than an inside diameter of the inner lumen of the puncture device, and wherein the distal portion of the retainer main body is more flexible than other portions of the retainer main body.

17. The system according to claim 14, wherein the distal portion of the retainer main body is more flexible than other portions of the retainer main body.

18. A method for retaining a cylindrical shape of an elongated catheter inserted into a living body, the method comprising:

piercing a living body with a puncture device;

inserting a catheter assembled with a catheter shape retainer to retain the cylindrical shape of the catheter into an inner lumen of the puncture device; and wherein the catheter shape retainer including a retainer main body and a movement restrictor disposed closer to a distal portion of the retainer main body than a proximal portion of the retainer main body to restrict the catheter from moving toward the proximal portion of the retainer main body over the movement restrictor, and when a portion of the retainer main body including the distal portion of the retainer main body is inserted into the living body, a portion of the retainer main body located outside of the living body has a length longer than a total length of the puncture device.

* * * * *